United States Patent
Fukuda et al.

(10) Patent No.: US 10,881,338 B2
(45) Date of Patent: Jan. 5, 2021

(54) BIOLOGICAL INFORMATION DETECTION APPARATUS AND BIOLOGICAL INFORMATION DETECTION METHOD

(71) Applicant: HITACHI, LTD., Tokyo (JP)

(72) Inventors: Nobuhiro Fukuda, Tokyo (JP); Masashi Kiguchi, Tokyo (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 16/414,280

(22) Filed: May 16, 2019

(65) Prior Publication Data
US 2019/0350505 A1 Nov. 21, 2019

(30) Foreign Application Priority Data
May 21, 2018 (JP) ................. 2018-096701

(51) Int. Cl.
*A61B 5/00* (2006.01)
*A61B 5/1455* (2006.01)
*H04N 5/33* (2006.01)
*G06T 7/90* (2017.01)
*G06T 7/00* (2017.01)

(52) U.S. Cl.
CPC ........ *A61B 5/14552* (2013.01); *A61B 5/0075* (2013.01); *G06T 7/0012* (2013.01); *G06T 7/90* (2017.01); *H04N 5/33* (2013.01); *A61B 2562/0233* (2013.01);
(Continued)

(58) Field of Classification Search
CPC ........ A61B 5/14552; A61B 2562/0233; A61B 5/0077; A61B 5/0075; H04N 5/33; H04N 5/2258; H04N 5/332; G06T 7/90; G06T 7/0012; G06T 2207/10048; G06T 2207/30101; G06T 2207/10024;
(Continued)

(56) References Cited

U.S. PATENT DOCUMENTS

2019/0167124 A1* 6/2019 Verkruijsse .......... A61B 5/7221

FOREIGN PATENT DOCUMENTS

JP 2012-239661 A 12/2012

OTHER PUBLICATIONS

Verkruysse et al., "Remote plethysmographic imaging using ambient light,", Optics express 16.26 (2008): 21434-21445.

* cited by examiner

*Primary Examiner* — Tony Ko
(74) *Attorney, Agent, or Firm* — Volpe Koenig

(57) ABSTRACT

A biological information detection apparatus for measuring a $SpO_2$ without contact from a distant position includes a camera that acquires an image with visible and infrared light, a first wavelength fluctuation detection section detects a temporal variation of a wavelength of an image with the visible light to generate a first wavelength difference data signal, a first amplitude detection section detects an amplitude of the first wavelength difference data signal, a second wavelength fluctuation detection section detects a temporal variation of a wavelength of an image with the infrared light to generate a second wavelength difference data signal, a second amplitude detection section detects an amplitude of the second wavelength difference data signal, a ratio calculation section calculates a ratio between the amplitudes of the first and second wavelength difference data signals, and an oxygen saturation concentration calculation section calculates an oxygen saturation concentration based on the calculated amplitude ratio.

9 Claims, 17 Drawing Sheets

(52) U.S. Cl.
CPC ........... *G06T 2207/10024* (2013.01); *G06T 2207/10048* (2013.01); *G06T 2207/30101* (2013.01)

(58) Field of Classification Search
CPC . G06T 2207/10016; G06T 2207/30104; G06T 7/0016
See application file for complete search history.

FIG.13

| RATIO SIGNAL | OXYGEN SATURATION CONCENTRATION |
|---|---|
| 1.0 | 100% |
| 1.1 | 95% |
| 1.2 | 90% |
|  | . |
|  | . |
| 2.0 | 30% |

# BIOLOGICAL INFORMATION DETECTION APPARATUS AND BIOLOGICAL INFORMATION DETECTION METHOD

FIELD OF THE INVENTION

The present disclosure relates to a technology for detecting information relating to a biological body.

BACKGROUND OF THE INVENTION

A pulse oximeter is available as medical equipment used for decision of a degree of severity of pneumonia, respiratory failure, heart failure and so forth. The pulse oximeter is contact type equipment that is mounted on a fingertip and irradiates infrared light (IR) and red light on a finger from above to measure an absorption amount of hemoglobin by a sensor to acquire an arterial blood oxygen saturation ($SpO_2$).

In recent years, as a technique for acquiring biological information, a technology is available by which biological information can be detected on the real time with non-contact using a microwave or a camera. Especially, in pulse detection using a camera, downsizing of a camera module is advanced in recent years, and the camera module is incorporated in a portable terminal including a smartphone and is spread.

As a technology for performing pulse detection by imaging, a technique is available that a G signal is traced especially from among red, green, blue (RGB) signals in a face image to detect a pulse (Verkruysse, Wim, Lars O. Svaas and, J. Stuart Nelson, "Remote plethysmographic imaging using ambient light.", Optics express 16. 26 (2008): 21434-21445.). Further, a technique is available that a pulse signal is specified from a spectral distribution of a time series signal (JP-2012-239661-A).

SUMMARY OF THE INVENTION

The technology described above is expected as a measurement technique that does not impose a load on a subject. Under such circumstances, as a technology for monitoring a condition sudden change of a driver during driving or an elderly at home by respiratory disease, heart failure or the like, a technology is important that the $SpO_2$ is measured with non-contact from a distant position using a camera.

According to an aspect of the present disclosure, there is provided a biological information detection apparatus including a camera that acquires an image with visible light and infrared light, a first wavelength fluctuation detection section that detects a temporal variation of a wavelength of an image with the visible light to generate a first wavelength difference data signal, a first amplitude detection section that detects an amplitude of the first wavelength difference data signal, a second wavelength fluctuation detection section that detects a temporal variation of a wavelength of an image with the infrared light to generate a second wavelength difference data signal, a second amplitude detection section that detects an amplitude of the second wavelength difference data signal, a ratio calculation section that calculates a ratio between the amplitude of the first wavelength difference data signal and the amplitude of the second wavelength difference data signal, and an oxygen saturation concentration calculation section that calculates an oxygen saturation concentration based on the calculated ratio between the amplitudes.

According to another aspect of the present disclosure, there is provided a biological information detection method including a first step of acquiring an image with visible light, a second step of acquiring an image with infrared light, a third step of detecting a temporal variation of a wavelength of an image with the visible light to generate a first wavelength difference data signal, a fourth step of detecting an amplitude of the first wavelength difference data signal, a fifth step of detecting a temporal variation of a wavelength of an image with the infrared light to generate a second wavelength difference data signal, a sixth step of detecting an amplitude of the second wavelength difference data signal, a seventh step of calculating a ratio between the amplitude of the first wavelength difference data signal and the amplitude of the second wavelength difference data signal, and an eighth step of estimating information of a biological body based on the calculated ratio between the amplitudes.

With the present disclosure, a technology can be provided that measures a $SpO_2$ with non-contact from a distant position using a camera.

BRIEF DESCRIPTION OF THE DRAWINGS

FIG. 13 is a view depicting an example of a table indicative of a relationship between a ratio signal and an oxygen saturation concentration;

DESCRIPTION OF THE PREFERRED EMBODIMENTS

Figure 1:
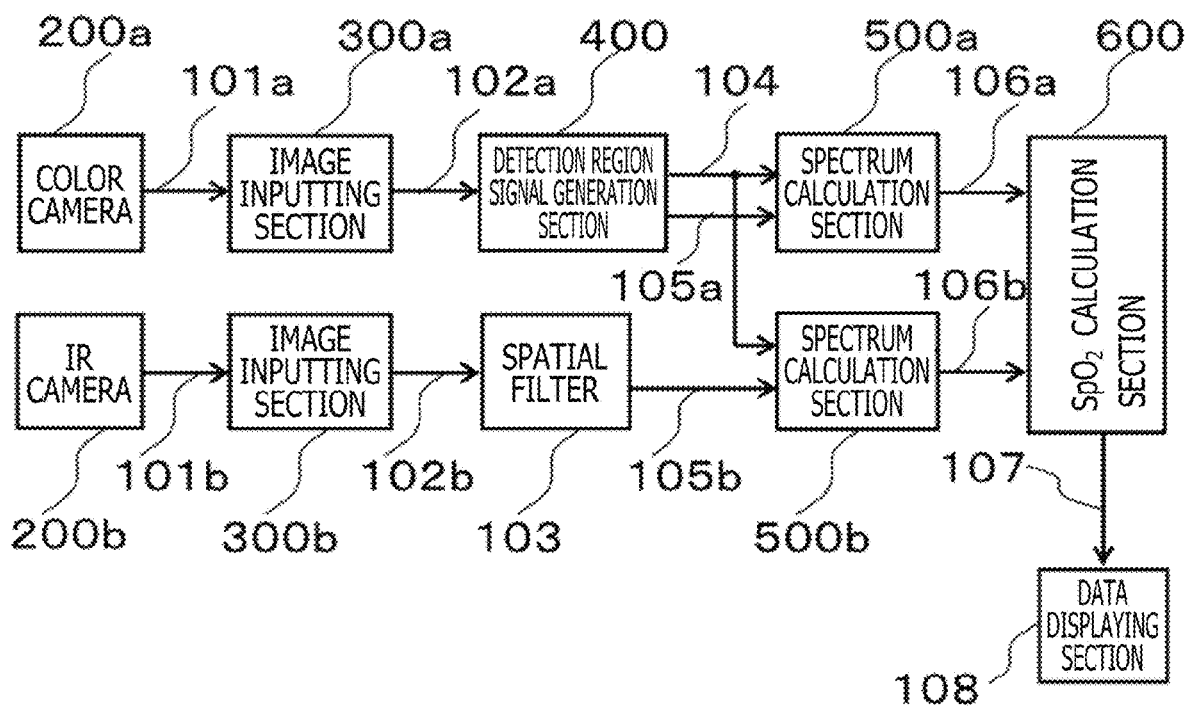
FIG. 1 is a block diagram of a biological information detection apparatus of an embodiment 1.

In the following, while embodiments of the present disclosure are described with reference to the drawings, the present disclosure is not necessarily limited to the embodiments. It is to be noted that like elements in the drawings depicting the embodiments are denoted by like reference characters and overlapping description of them is omitted.

In the case where there are a plurality of elements having same or similar functions, a different subscription (for example, an alphabet) is sometimes attached to a same reference character (for example, a numeral) in the description. However, in the case where a plurality of elements need not be distinguished from each other, the subscription is sometimes omitted for the description.

Representations of "first," "second," "third" and so forth in the present specification are attached for the identification of the components, and do not necessarily limit the number, the order or the contents of the components. Further, the number for identifying a component is used for each context, and a number used in one context does not always indicate a same configuration in a different context. Further, a component identified by a certain number does not prevent the component from having a function of a different component identified by a different number.

The position, size, shape, range and so forth of each component depicted in the drawings do not necessarily represent an actual position, size, shape, range and so forth in order to facilitate understandings of the disclosure. Therefore, the disclosure is not necessarily limited in terms of the position, size, shape, range and so forth disclosed in the drawings and so forth.

An example among embodiments hereinafter described in detail uses infrared and visible light image signals obtained by imaging. The example includes, for each of the infrared and visible light image signals, a spectrum detection section that in turn includes a wavelength fluctuation detection section that detects a fluctuation of an image from an inter-frame difference from an image signal preceding by one frame and a pulse wave detection section that estimates a pulse wave from the detected fluctuation and calculates an amplitude of the pulse wave. The example further includes a SpO₂ calculation section that calculates the ratio in magnitude between the generated two pulse waves and converts the ratio into an arterial blood oxygen saturation with reference to a correlation table that indicates a relationship between the calculated amplitude ratio and an oxygen saturation concentration, and makes contactless measurement possible.

Embodiment 1

The present embodiment is an example of a biological information detection apparatus that detects a SpO₂ from a face image using a camera. Although the face image in the present embodiment is a region decided as the face of a person, in order to measure the SpO₂, an image of a different part such as a hand or an arm may be used for detection. The region also may be an exposed region of an animal's skin other than a person's. The region for measurement is sometimes referred to as "face region," "face region or the like" for the convenience of description.

FIG. 1 is a block diagram of a biological information detection apparatus according to the present embodiment. The biological information detection apparatus according to the present embodiment includes a color camera 200a and an infrared (IR) camera 200b.

A first image inputting section 300a is connected to the color camera 200a. The first image inputting section 300a receives a color imaging data signal 101a as an input signal thereto and outputs a delayed color data signal 102a. The first image inputting section 300a is connected to a detection region signal generation section 400. The detection region signal generation section 400 receives the delayed color data signal 102a as an input thereto. The detection region signal generation section 400 outputs a first wavelength data signal (color signal) 105a and a level signal 104 to a first spectrum calculation section 500a.

A second image inputting section 300b is connected to the IR camera 200b. The second image inputting section 300b receives an IR imaging data signal 101b as an input thereto and outputs a delayed IR signal 102b. The second image inputting section 300b is connected to a spatial filter 103. The spatial filter 103 receives the delayed IR signal 102b, which has a line delay corresponding to taps of a convolution kernel, as an input thereto, weighted averages, for example, pixels around a noticed pixel and outputs a smoothed second wavelength data signal (IR signal) 105b.

The first wavelength data signal 105a and the level signal 104 are inputted to a second spectrum calculation section 500b. A first amplitude signal (color signal) 106a that is an output of the first spectrum calculation section 500a and a second amplitude signal (IR signal) 106b that is an output of the second spectrum calculation section 500b are inputted to a SpO₂ calculation section 600. The SpO₂ calculation section 600 calculates a SpO₂ and displays a result of the calculation on a data displaying section 108.

Each camera 200 may be, for example, a general camera that uses a solid-state imaging element. The data displaying section 108 may be, for example, a general liquid crystal display. The cameras 200, image inputting sections 300, detection region signal generation section 400, spatial filter 103, spectrum calculation sections 500a and 500b, and SpO₂ calculation section 600 other than the optical system can be achieved by a computer (not depicted) that executes software to perform intended control. As an alternative, functions equivalent to the functions achieved by the software can be implemented also by hardware such as an Field Programmable Gate Array (FPGA), an Application Specific Integrated Circuit (ASIC) or the like. The biological information detection apparatus further includes a storage device (not depicted) such as a semiconductor memory for storage and execution of software and execution.

Figure 2A:
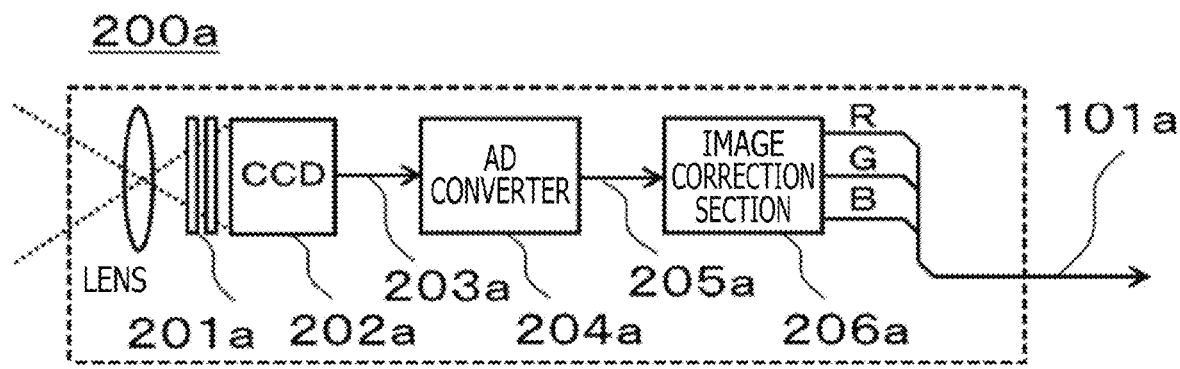
FIG. 2A is a block diagram depicting an example of a color camera module in the embodiment 1.

FIG. 2A is a view depicting an example of the color camera 200a of FIG. 1. In the color camera 200a, light passing through the lens is decomposed, for example, into light of three colors of RGB by a filter (IR cut filter and color filter) 201a and irradiated upon a charge coupled device (CCD) device 202a. While the color filter here is described as an RGB (red, green and blue) filter, it may otherwise be a YCM (yellow, cyan and magenta) filter having a complementary color relationship. An electric signal 203a obtained by photoelectric conversion of this light is digitalized by an Analog Digital (AD) converter 204a. A RAW data signal 205a that remains in the digitalized form is inputted to an image correction section 206a. The image correction section 206a outputs a color imaging data signal 101a that has, for example, RGB components for each one pixel. Although the color components here are described as RGB, they may otherwise be YCbCr or the like of color difference signals.

Figure 2B:
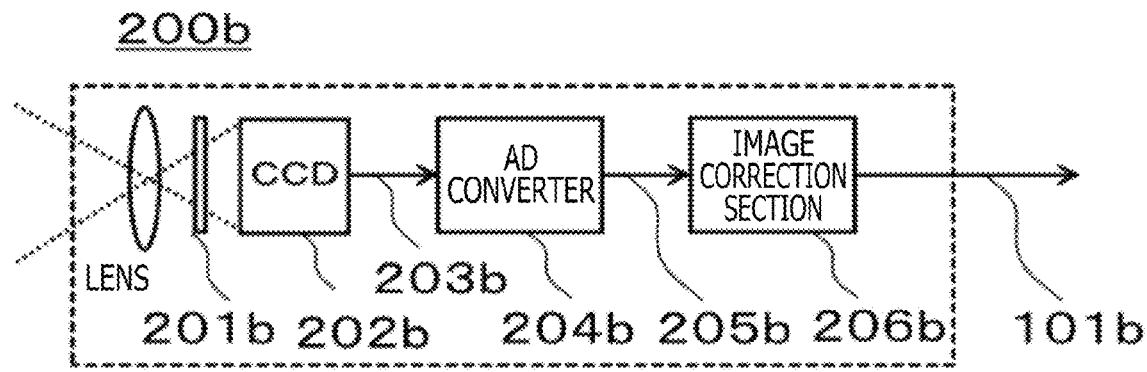
FIG. 2B is a block diagram depicting an example of an IR camera module in the embodiment 1.

FIG. 2B is a view depicting an example of the IR camera 200b of FIG. 1. In the IR camera 200b, light passing through the lens passes a filter (band pass filter or low pass filter) 201b, and, for example, infrared light is irradiated upon a CCD device 202b. An electric signal 203b obtained by photoelectric conversion of this light is digitalized by an AD converter 204b. A RAW data signal 205b that remains in the digitalized form is inputted to an image correction section 206b. The image correction section 206b outputs an IR imaging data signal 101b having IR light for each one pixel as a component.

Figure 3:
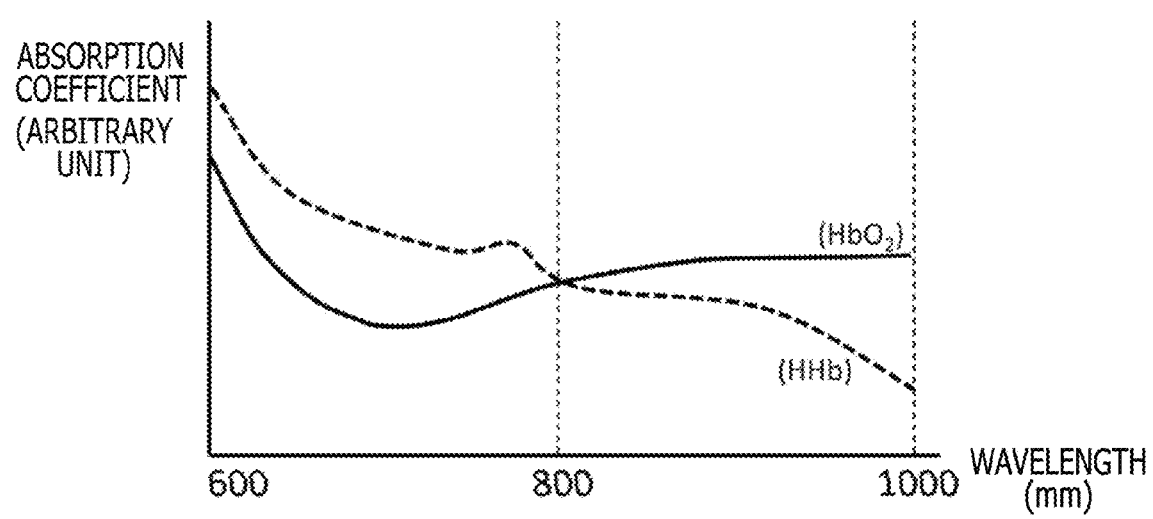
FIG. 3 is a graph illustrating absorption of hemoglobin in red wavelength to near infrared wavelength bands.

FIG. 3 is a view illustrating absorption of hemoglobin in the blood in red to infrared wavelength bands. A graph relating to oxygenated hemoglobin $HbO_2$ is indicated by a solid line, and a curve relating to reduced hemoglobin HHb is indicated by a broken line. As depicted in FIG. 3, in regard to the absorption coefficient on the red side at wavelengths equal to or shorter than 800 nm, HHb is higher than $HbO_2$. In order to detect the difference in absorption between them, it is desirable for the filter 201b of the IR camera 200b to pass a frequency band higher than the wavelength of 800 nm.

If red light is irradiated upon the blood, then since the absorption is low by oxygenated hemoglobin $HbO_2$, the amount of light received by the CCD device 202a is great. On the other hand, since the absorption is high by reduced hemoglobin HHb, the amount of light received by the CCD device 202a is small. Therefore, if the oxygenated hemoglobin $HbO_2$ increases and the reduced hemoglobin HHb decreases in a biological body, then the amount of red light received by the CCD device 202a increases.

On the other hand, in regard to infrared light, since the absorption is low by the reduced hemoglobin HHb, the amount of light received by the CCD device 202b is great. On the other hand, since the absorption is high by the oxygenated hemoglobin $HbO_2$, the amount of light received by the CCD device 202b is small. Therefore, if the oxygenated hemoglobin $HbO_2$ increases and the reduced hemoglobin HHb decreases in a biological body, then the amount of red light received by the CCD device 202b decreases.

In this manner, the state of the oxygenated hemoglobin $HbO_2$ and the reduced hemoglobin HHb is reflected on the electric signals 203a and 203b. Therefore, the ratio between the oxygenated hemoglobin $HbO_2$ and the reduced hemoglobin HHb, namely, the oxygen saturation, can be estimated from the ratio between the electric signals 203a and 203b. The foregoing is a basic principle of a pulse oximeter. The blood sent out from the heart moves in the form of a pulse wave in a blood vessel. In the pulse oximeter, a transmission light signal detected thereby exhibits a periodical intensity variation in accordance with a variation of the thickness of the pulsating arterial blood.

Figure 4:
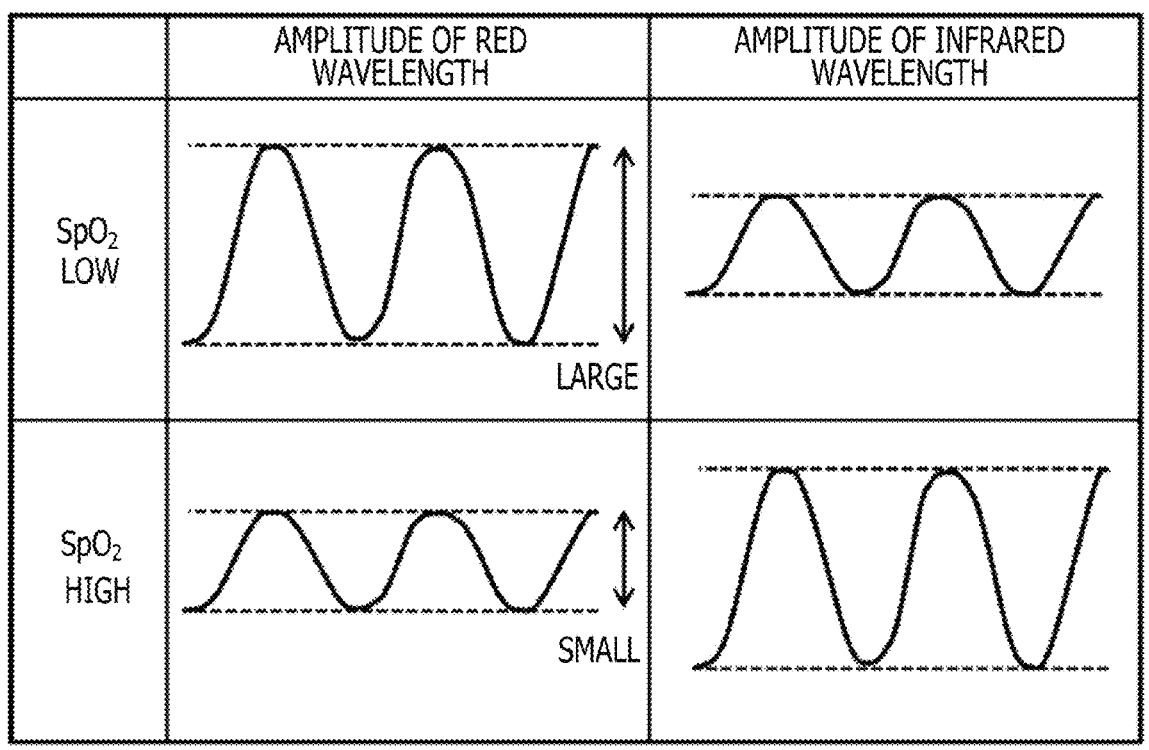
FIG. 4 is a table illustrating a relationship between an amplitude in red wavelength to near infrared wavelength bands and $SpO_2$.

FIG. 4 is a view illustrating a relationship between the amplitude of detection signals of red and infrared wavelengths and $SpO_2$. In response to pulsation of the cardiovascular system of a biological body, especially of the artery, the intensity of reflection or transmission light of the biological body pulsates. Upon such pulsation, the amplitude of the detection signals varies depending upon the oxygen saturation of the biological body and the wavelength of the light. As depicted in FIG. 4, the wavelength differs depending upon the wavelength such that, in the case where the value of the $SpO_2$ is low, the relationship of "red wavelength amplitude>infrared wavelength amplitude" is satisfied, but in the case where the value of $SpO_2$ is high, the relationship of "red wavelength amplitude<infrared wavelength amplitude" is satisfied. Utilizing this nature, the "red wavelength amplitude/infrared wavelength amplitude" is utilized as an indicator for the determination of the $SpO_2$.

Although the pulse oximeter utilizes the amplitude of a signal waveform by an intensity variation of transmission light as described above, in the present embodiment, in order to make contactless detection possible, a signal wavelength is obtained from a color variation of an imaged biological body (wavelength fluctuation) to detect an amplitude.

Figure 5:
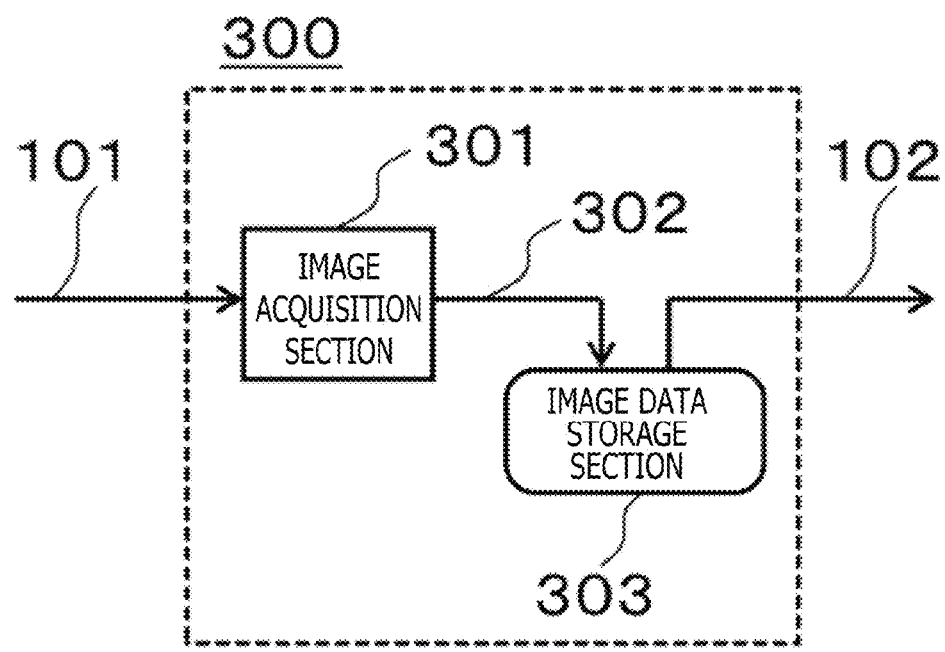
FIG. 5 is a block diagram illustrating an example of an image inputting section in the embodiment 1.

FIG. 5 is a view depicting an example of each image inputting section 300 of FIG. 1. In the case of the first image inputting section 300a, it includes an image acquisition section 301a that receives the color imaging data signal 101a as an input signal and outputs an RGB signal 302a of an image. The first image inputting section 300a further includes an image data storage section 303a that receives the RGB signal 302a for one frame as an input signal thereto and outputs a delayed color data signal 102a, for example, of RGB or the like. In the case of the second image inputting section 300b for IR, it may use an IR imaging data signal 101b in place of the color imaging data signal 101a and use a delayed IR signal 102b in place of the delayed color data signal 102a.

Figure 6:
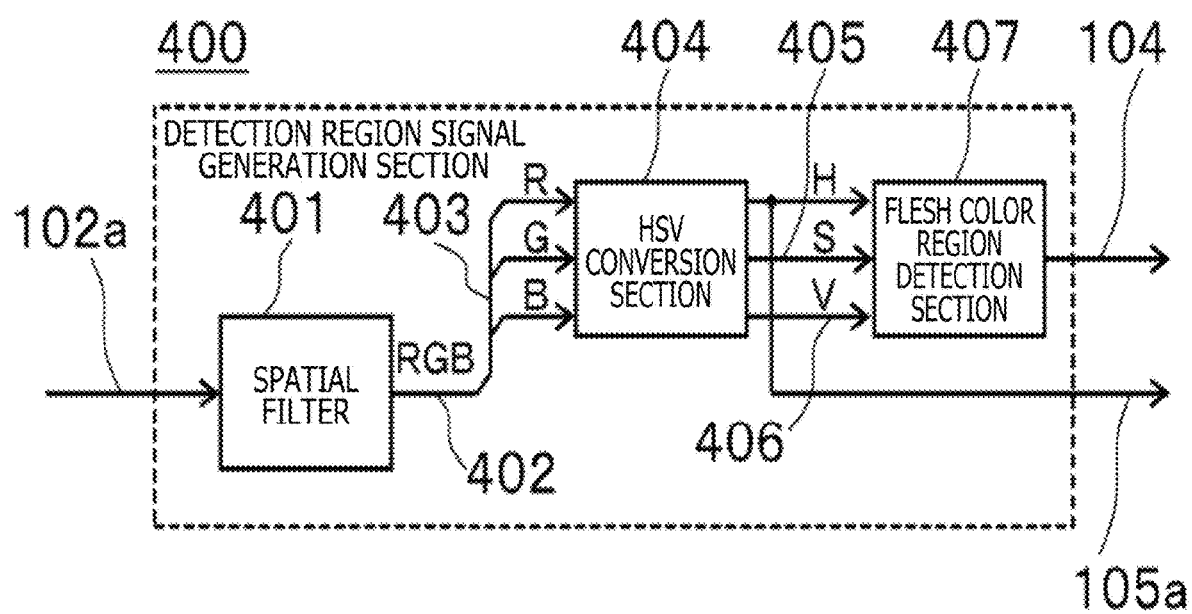
FIG. 6 is a block diagram depicting an example of a detection region signal generation section in the embodiment 1.

FIG. 6 is a view depicting an example of the detection region signal generation section 400 of FIG. 1. The detection region signal generation section 400 performs an image process for each pixel. The detection region signal generation section 400 includes a spatial filter 401 that receives, as an input thereto, a delayed color data signal 102a having a line delay corresponding to taps of a convolution kernel and weighted averages the delayed color data signal 102a, for example, around a noticed pixel and outputs a smoothed RGB signal 402. The detection region signal generation section 400 further includes an HSV conversion section 404 that receives an unpack signal 403 formed by decomposing the smoothed RGB signal 402 into R, G and B signals as an input thereto and converts the unpack signal 403 into an H signal (hue), namely, a first wavelength data signal (color signal) 105a, an S signal (saturation) 405 and a V signal (value) 406. Further, the detection region signal generation section 400 includes a flesh color region detection section 407 that receives the H signal (hue) 105a, S signal (saturation) 405 and V signal (value) 406 as inputs thereto and outputs a level signal 104 indicative of a flesh color region.

Figure 7:
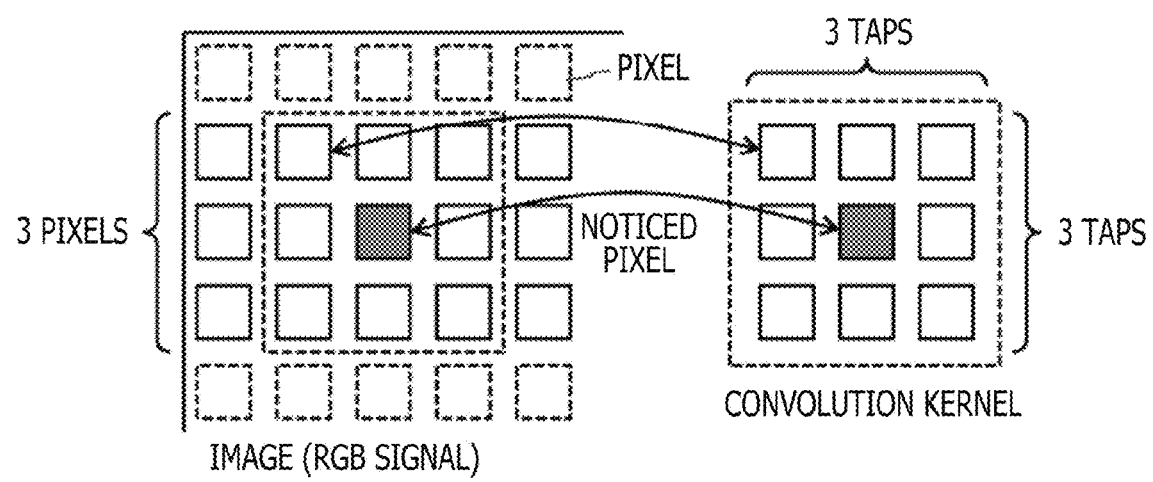
FIG. 7 is a schematic view illustrating a concept of operation of a spatial filter in the embodiment 1.

FIG. 7 is a view illustrating an example of a process of the spatial filter 401 depicted in FIG. 6. The spatial filter 401 generally weights luminances of a central pixel and surrounding pixels, performs product sum arithmetic operation or non-linear arithmetic operation and determines a resulting value as a value of the center pixel. FIG. 7 depicts an example in which a convolution kernel of three taps vertically and horizontally, namely, a 3×3 convolution kernel, is applied to an image, and a value obtained by convolution arithmetic operation of the 3×3 convolution kernel centered at the noticed pixel of the image becomes the smoothed RGB signal 402. Values of the kernel are coefficients for weighted averaging, and only it is sufficient if the sum value of the values becomes 1.0. Further, the smoothing may be performed so as to obtain an average value distribution or a Gaussian distribution.

By the smoothing process by the spatial filter 401, the influence of noise in the image can be reduced. For example, since a biological body during imaging is not stationary, preceding and succeeding images do not coincide with each other in a unit of a pixel. Therefore, since a hair or dust makes a kind of noise, to spatially smoothen (average) an image is effective in detection of information by color change after a wavelength fluctuation detection section 550 hereinafter described.

Figure 8:
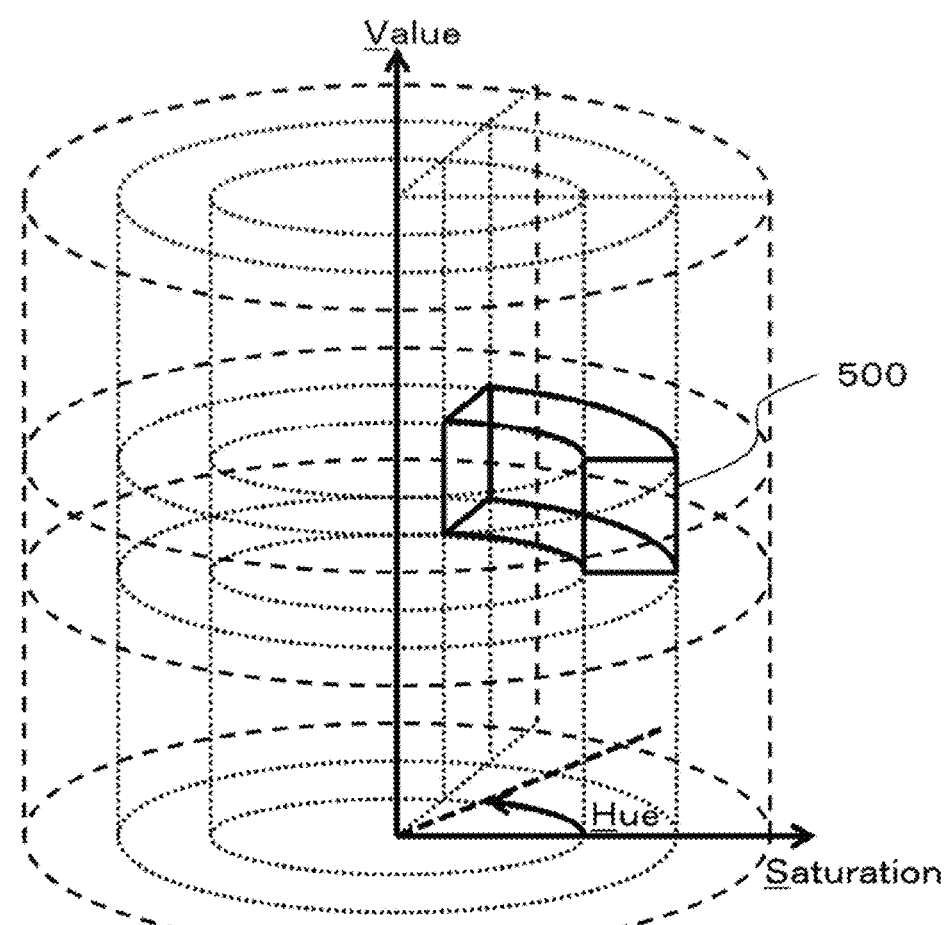
FIG. 8 is a conceptual diagram depicting a designation range in a hue, saturation and value (HSV) color space and a partial color space.

FIG. 8 is a view depicting a designation range of an HSV color space and a partial color space by the HSV conversion section 404 in FIG. 6. FIG. 8 represents an HSV color space in a cylinder coordinate system. The axis of ordinate is Value, namely, the value and represents brightness of color, and the axis in a radial direction is Saturation, namely, saturation and represents color depth. A rotation angle is Hue, namely, hue. The hue is independent of the strength and darkness, and if it is considered that a captured image catches reflection of light, then it is considered that the hue corresponds to a wavelength component of the reflection light. Similarly, it can be considered that the value indicates the strength of a specific wavelength. It is to be noted that the flesh color region detection section 407 designates a flesh color region using a partial color space like a partial color space 500 in FIG. 8 in the HSV color region, and it is sufficient if, in the case where the HSV value is included in the flesh color region, "1" is set, but in the case where the HSV value is not included in the flesh color region, "0" is set, to the level signal 104.

As a setting method of a partial color space, for example, zero degrees=360 degrees of the hue is set as red, 120 degrees as green and 240 degrees as blue, and a section designated by a color 1 and another color 2 is designated as the applicable range. Meanwhile, as regards the saturation, 0% is set as a pale color, and 100% as a deep color, and as regards the value, 0% is set as a dark color, and 100% as a bright color. Thus, a range is designated similarly.

The flesh color region detection section 407 can decide whether or not the applicable pixel is a portion of a human skin in such a manner as described above. It is to be noted that, in the present specification, a region that is decided as part of a human skin by the flesh color region detection section 407 and is configured from pixels whose level signal 104 is "1" is referred to as flesh color region. Although the term "flesh color" is used for the flesh color region because the flesh color region can be designated arbitrarily by the range designation described above, the flesh color region is not necessarily restricted to a specific color. Generally, a region that is suitable to acquire biological information and corresponds to a color of an exposed skin of a person or an animal is detected.

Figure 9:
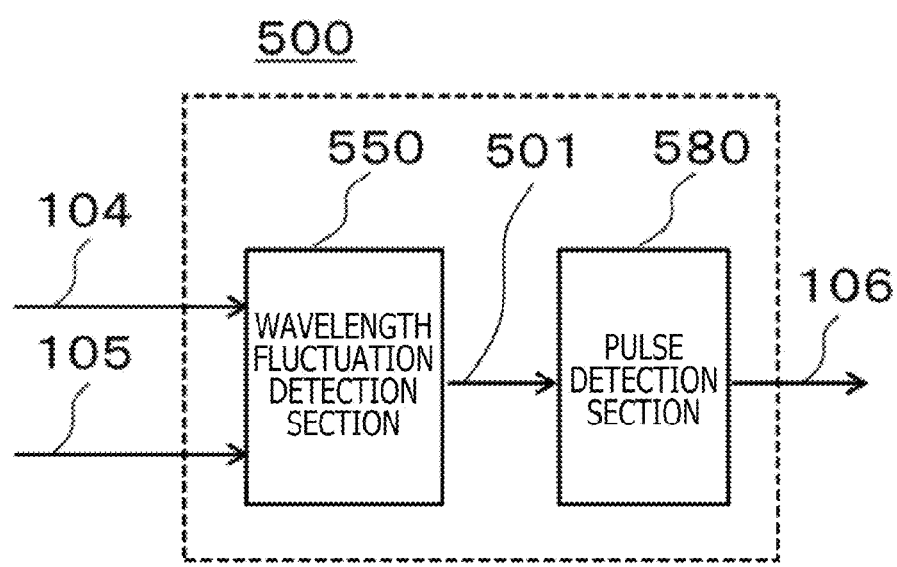
FIG. 9 is a block diagram depicting an example of a spectrum calculation section in the embodiment 1.

FIG. 9 is a view depicting an example of each spectrum calculation section 500. The first spectrum calculation section 500a includes a wavelength fluctuation detection section 550 that receives the level signal 104 and the first wavelength data signal (color signal) 105a as inputs thereto and outputs an integration wavelength difference data signal 501a, and a first pulse detection section 580a that receives the integration wavelength difference data signal 501a as an input thereto and outputs a first amplitude signal (color signal) 106a. Meanwhile, in the second spectrum calculation section 500b for an IR signal, it is sufficient if the first wavelength data signal (color signal) 105a is replaced by a second wavelength data signal (IR signal) 105b and the first amplitude signal (color signal) 106a is replaced by a second amplitude signal (IR signal) 106b.

Figure 10:
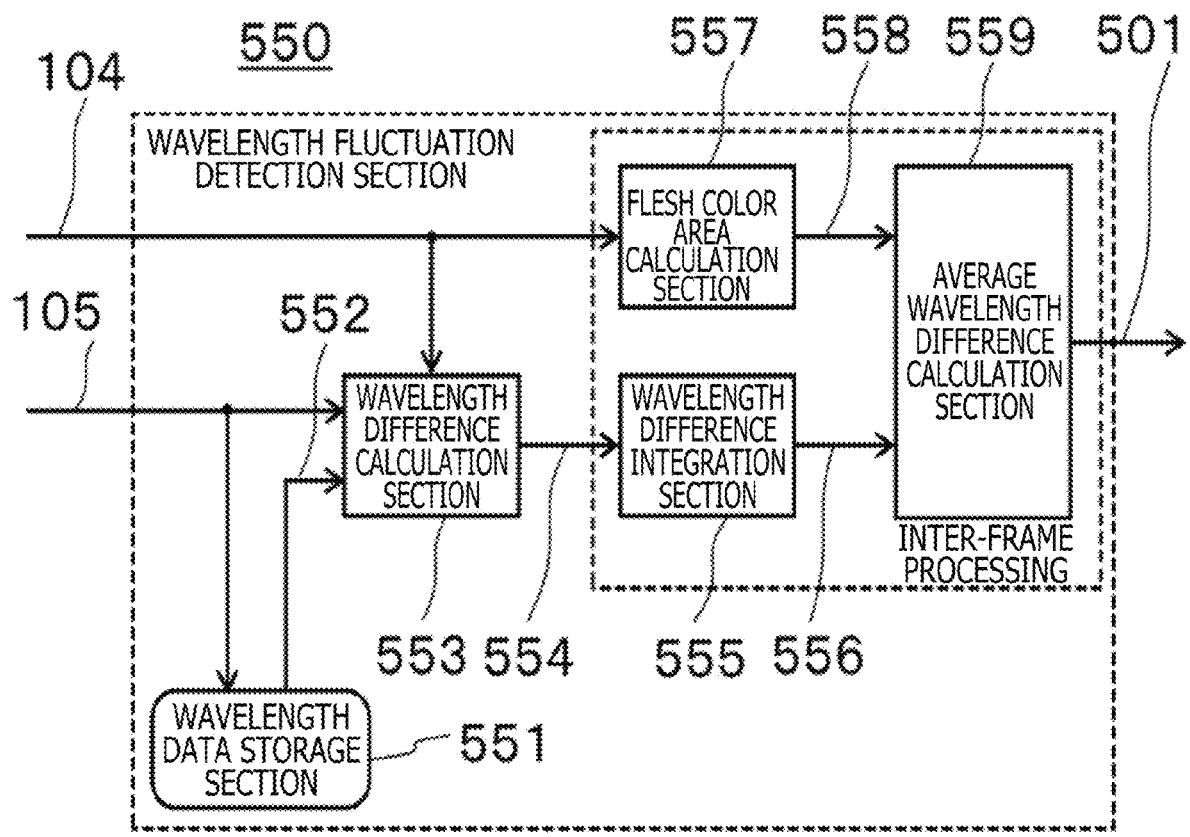
FIG. 10 is a block diagram depicting an example of a wavelength fluctuation detection section in the embodiment 1.

FIG. 10 is a view depicting an example of the wavelength fluctuation detection section 550 of FIG. 9. The wavelength fluctuation detection section 550 detects an average variation in color in a region of a flesh color of an imaging object. The wavelength fluctuation detection section 550 of the first spectrum calculation section 500a includes a wavelength data storage section 551a, a wavelength difference calculation section 553a, a flesh color area calculation section 557, a wavelength difference integration section 555a and an average wavelength difference calculation section 559a.

The wavelength difference calculation section 553a receives a level signal 104 indicative of a flesh color region and a first wavelength data signal (color signal) 105a as inputs thereto. Further, the wavelength difference calculation section 553a stores the first wavelength data signal 105a for each frame into a wavelength data storage section 551a thereof and receives a frame-delayed delay wavelength data signal 552a from the wavelength data storage section 551a as an input thereto. The wavelength difference calculation section 553a outputs a wavelength difference data signal 554a between the first wavelength data signal 105a and the delay wavelength data signal 552a in regard to the pixels in the flesh color region and outputs the "0" value in regard to the outside of the flesh color region.

The flesh color area calculation section 557a receives a level signal 104 indicative of a flesh color region as an input thereto, and counts the number of pixels in the flesh color region for each frame and outputs a flesh color area signal 558a.

The wavelength difference integration section 555a receives the wavelength difference data signal 554a of the pixels in the flesh color region as an input thereto, and integrates a wavelength difference for each frame and outputs an integration wavelength difference data signal 556a.

The average wavelength difference calculation section 559a receives the flesh color area signal 558a and the integration wavelength difference data signal 556a as inputs thereto, and outputs an integration wavelength difference data signal 501 averaged in regard to all pixels in the flesh color region in one frame by division of the integrated wavelength difference data and the flesh color area.

In regard to the second wavelength fluctuation detection section 550b of the second spectrum calculation section 500b, it is sufficient if the first wavelength data signal (color signal) 105a is replaced into a second wavelength data signal (IR signal) 105b and the averaged integration wavelength difference data signal (color signal) 501a is replaced into an averaged integration wavelength difference data signal (IR signal) 501b.

Figure 11:
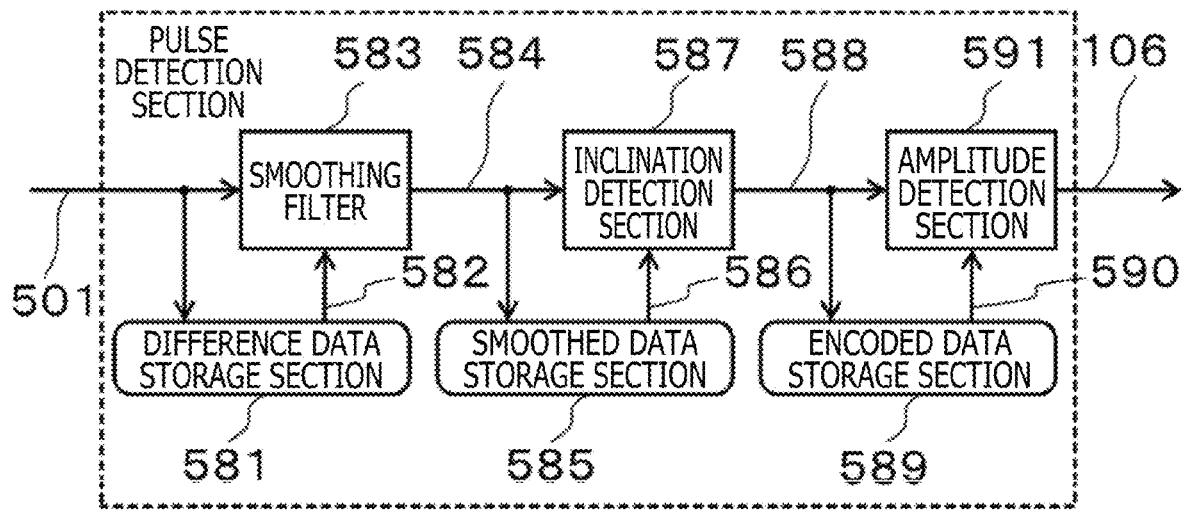
FIG. 11 is a block diagram depicting an example of a pulse detection section in the embodiment 1.

FIG. 11 is a view depicting an example of each pulse detection section 580 of FIG. 9. The pulse detection section 580 performs an image process for each frame. The pulse detection section 580 includes a smoothing filter 583, a difference data storage section 581, an inclination detection section 587, a smoothed data storage section 585, an amplitude detection section 591 and an encoded data storage section 589. Both of the first pulse detection section 580a and the second pulse detection section 580b may have configurations similar to each other.

The difference data storage section 581 receives the averaged integration wavelength difference data signal 501 as an input thereto and outputs a delayed wavelength difference data signal 582 having a predetermined delay.

The smoothing filter 583 receives the averaged integration wavelength difference data signal 501 and the delayed wavelength difference data signal 582 as inputs thereto and outputs a wavelength difference data signal 584 smoothed from wavelength data of a plurality of frames on a continuous time axis. The smoothing filter 583 is configured to block, for example, a frequency component sufficiently higher than an estimated frequency of a human pulse. This configuration removes noise in a detection signal.

The smoothed data storage section 585 receives the smoothed wavelength difference data signal 584 as an input thereto, and holds wavelength difference data of a plurality of frames and outputs a smoothed delayed wavelength difference data signal 586.

The inclination detection section 587 receives the smoothed wavelength difference data signal 584 and the smoothed delayed wavelength difference data signal 586 as inputs thereto and determines a difference between two successive frame data or between average frames of several successive neighboring frames to determine a sign of an inclination.

The encoded data storage section 589 receives an encoded data signal 588 from the inclination detection section 587 as an input thereof, holds encoded data for a plurality of frames and outputs a delayed encoded data signal 590.

The amplitude detection section 591 receives the encoded data signal 588 and the delayed encoded data signal 590 as inputs thereto, determines extremes by determining a frame with which the sign change of the inclination is a change from a positive value to a negative value as maximum frame and determining a frame with which the sign change of the inclination is a change from a negative value to a positive value as a minimum frame, and outputs, for example, a maximal value as a pulse signal 106. The pulse signal 106 corresponds, for example, to the amplitude of the waveform depicted in FIG. 4.

Since the smoothing filter 583 smoothens the integration wavelength difference data signal 501 in such a manner as described above, erroneous detection of the pulse arising from a fine fluctuation of a difference data signal caused by noise or the like can be prevented. Since the inclination detection section 587 detects a variation (inclination) of difference data between adjacent frames and the amplitude detection section 591 detects a maximal value or a minimal value of the difference data on the basis of a result of the detection by the inclination detection section 587, the amplitude can be measured with a high degree of accuracy. Further, in the case where the inclination detection section 587 is to determine the difference between average frames of a plurality of successive neighboring frames, erroneous detection of pulse can be prevented similarly to the smoothing filter.

Figure 12:
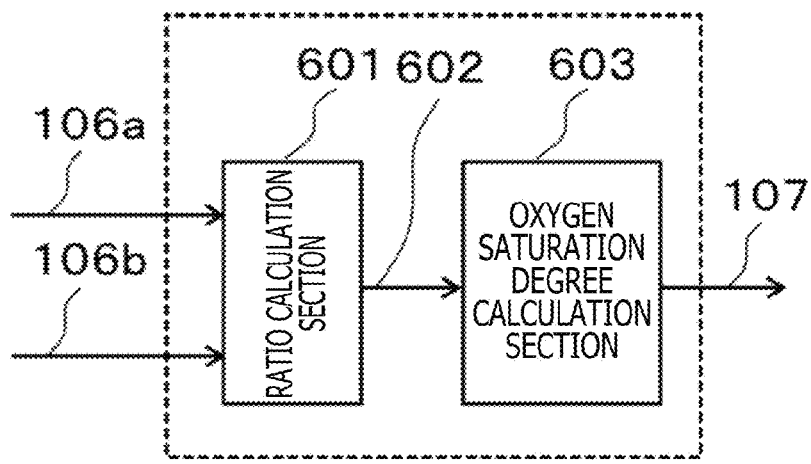
FIG. 12 is a block diagram illustrating an example of a $SpO_2$ detection section in the embodiment 1.

FIG. 12 is a view depicting an example of the SpO$_2$ calculation section 600 of FIG. 1. The SpO$_2$ calculation section 600 includes a ratio calculation section 601 and an oxygen saturation calculation section 603.

The ratio calculation section 601 receives the first amplitude signal (color signal) 106a and the second amplitude signal (IR signal) 106b as inputs thereto and output a zero signal when the first amplitude signal (color signal) 106a is zero but outputs, in any other case, a ratio signal 602 in accordance with a ratio such as an amplitude signal (color signal)/amplitude signal (IR signal), an amplitude signal (IR signal)/(amplitude signal (color signal)+amplitude signal (IR signal)) or the like.

The oxygen saturation calculation section 603 receives a ratio signal 602 from the ratio calculation section 601 as an input thereto and outputs a SpO$_2$ signal 107 associated, for example, by a correlation table with an oxygen saturation.

FIG. 13 depicts an example of the correlation table. The correlation table is stored into a memory that can be read from the oxygen saturation calculation section 603. As numerical values of the oxygen saturation of the correlation table, oxygen saturation values measured, for example, with blood taken from a biological body are associated with values of the ratio signal 602 measured with the applicable biological body. The value of the ratio calculation section 602 depends upon the sensitivity or the amplification factor of the apparatus.

According to the configuration described above, a monitoring technique can be provided which detects a sudden condition change by a respiratory disease, heart failure or the like of a subject with non-contact by SpO$_2$ detection using a camera.

Embodiment 2

The embodiment 1 described above is directed to the technology that pulses of red and infrared frequencies are detected from biological images of the face or the like using two cameras and the SpO$_2$ is determined by a ratio in amplitude. In the embodiment 2, a biological information detection apparatus that measures the SpO$_2$ with one camera is described.

In recent years, a camera has appeared which has pixels of four components per one pixel including a near infrared filter in addition to color components of, for example, RGB or the like. The present embodiment is directed to a technique that implements a biological information detection apparatus of a compact configuration using the camera just described.

Figure 14:
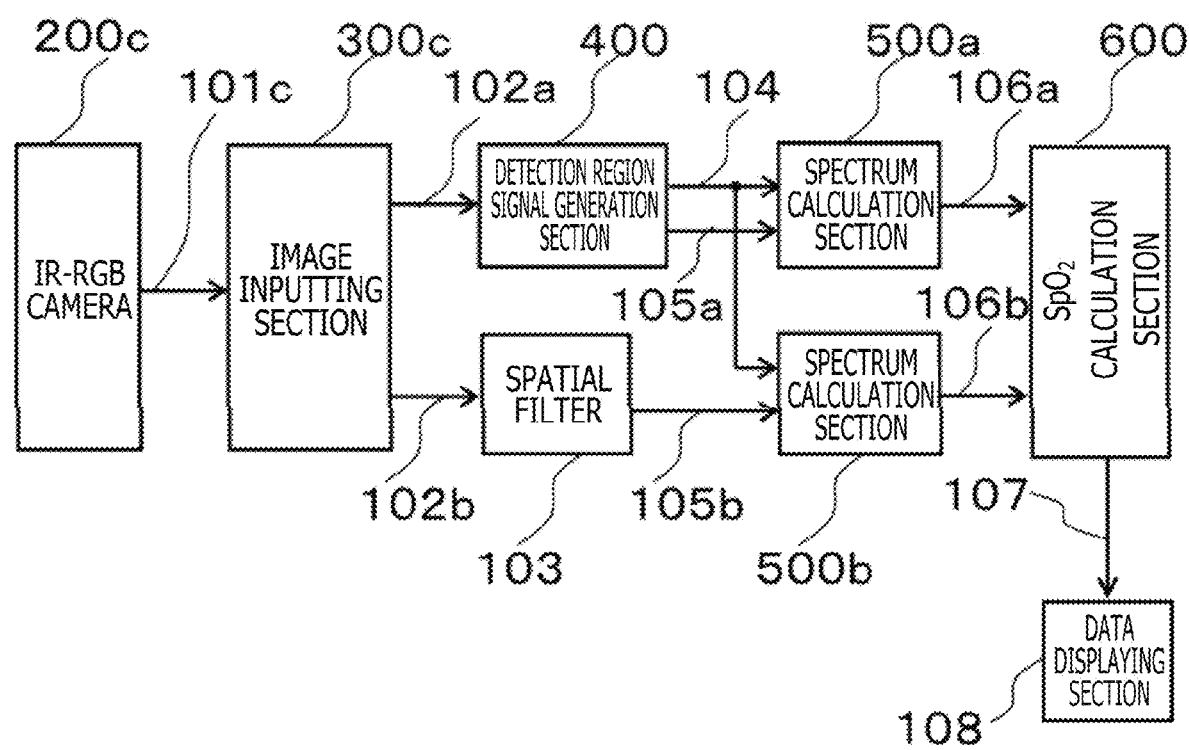
FIG. 14 is a block diagram of a biological information detection apparatus of an embodiment 2.

FIG. 14 is an example of a block diagram of the biological information detection apparatus according to the embodiment 2. In FIG. 14, like components to those of the example of FIG. 1 are denoted by like reference characters, and overlapping description of them is omitted herein. The biological information detection apparatus according to the present embodiment includes an IR-color camera 200c as a single camera and further includes an image inputting section 300c that receives an IR-color imaging data signal 101c as an input signal thereto.

Figure 15:
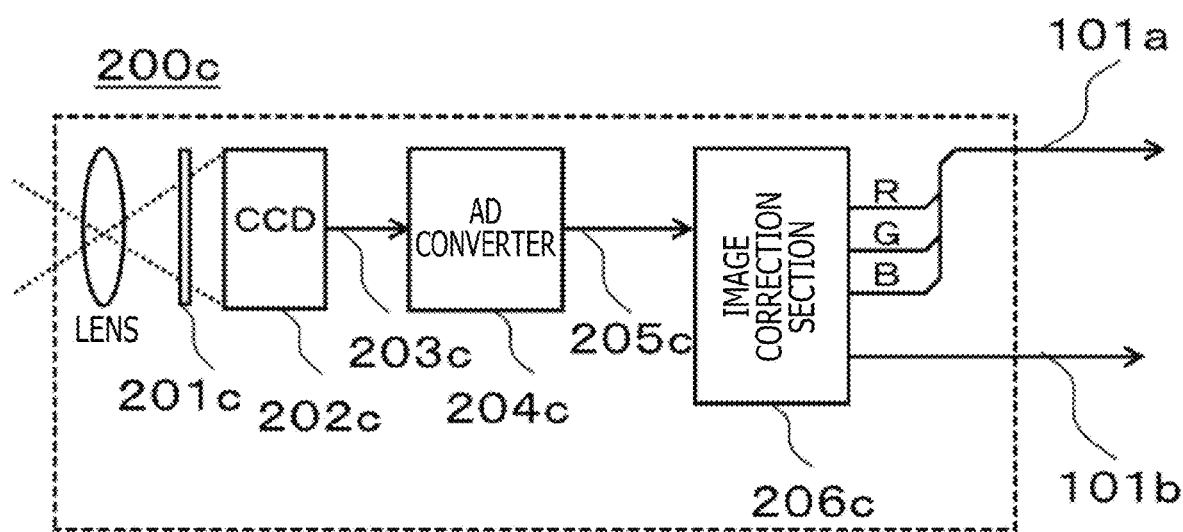
FIG. 15 is a block diagram depicting an example of an RGB-IR camera module in the embodiment 2.

FIG. 15 is a view depicting an example of the IR-color camera 200c of FIG. 14. In the IR-color camera 200c, light passing through the lens is decomposed, for example, into light of four colors of RGB and IR through a filter (IR-color filter) 201c and irradiated upon a CCD device 202c. While the color filter here is described as an RGB filter, it may otherwise be a yellow, cyan and magenta (YCM) filter having a complementary color relationship. An electric signal 203c obtained by photoelectric conversion of this light is digitalized by an AD converter 204c. A RAW data signal 205c that remains in the digitalized form is inputted to an image correction section 206c. The image correction section 206c outputs a color imaging data signal 101a that has, for example, RGB components for each one pixel and an IR imaging data signal 101b. The color imaging data signal 101a and the IR imaging data signal 101b are collectively referred to as IR-color imaging data signal 101c of FIG. 14. Although the color components are described as RGB, they may otherwise be YCbCr or the like of color difference signals.

According to the configuration described above, a technique can be provided which detects pulses of infrared and red wavelengths from a biological image of the face or the like using a single camera and detects the SpO$_2$ from a ratio in amplitude.

Embodiment 3

The embodiment 2 described above is directed to a technology that pulses of infrared and red wavelengths from a biological image of the face or the like using a single camera and detects SpO$_2$ from a ratio in amplitude. The embodiment 3 described below is directed to a biological information detection apparatus that performs correction of the $SpO_2$ with external light.

A general pulse oximeter can irradiate light normally in accordance with a same condition from light sources of an infrared wavelength and a red light wavelength. Also in the case of $SpO_2$ detection in which a camera technology described hereinabove in connection with the embodiments 1 and 2 is used, measurement can be performed in accordance with stable conditions by preparing an illumination. However, an environmental condition free from external light cannot always be prepared. Therefore, a technique that can correct with the value of external light is provided.

Figure 16:
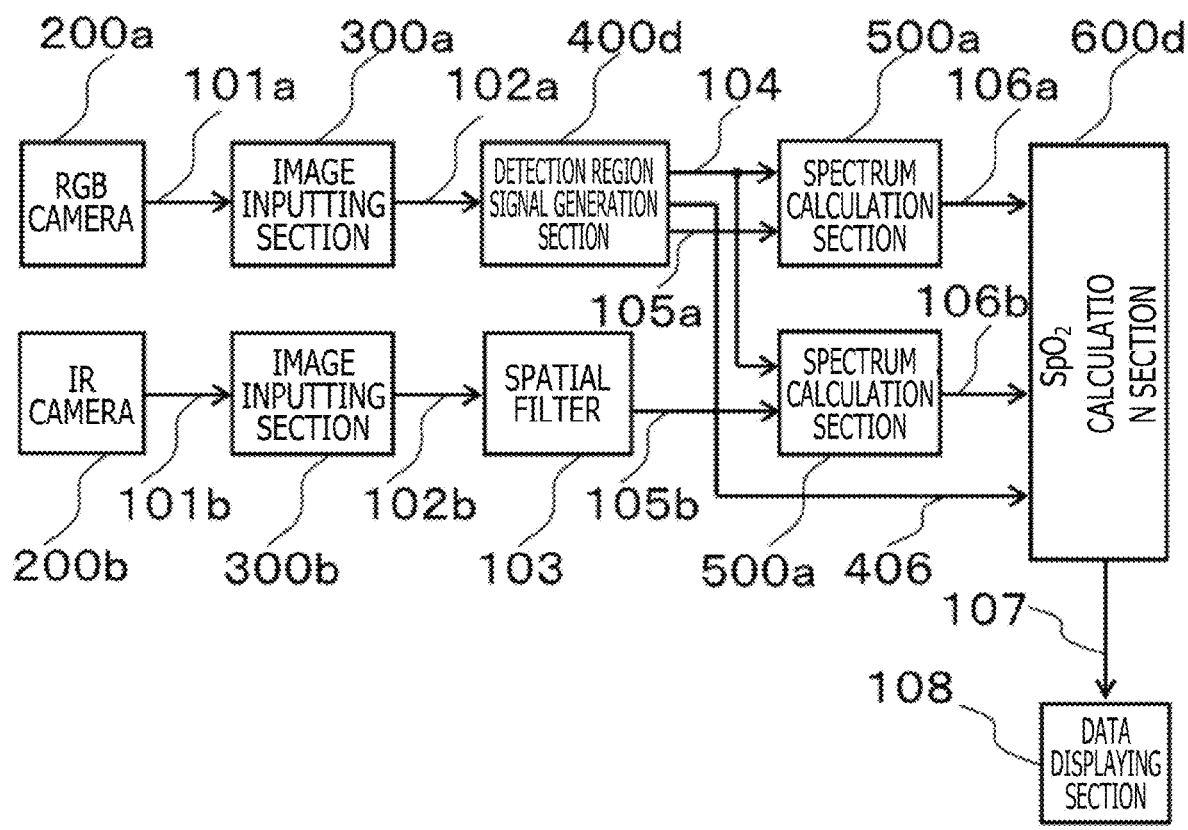
FIG. 16 is a block diagram of a biological information detection apparatus of an embodiment 3.

FIG. 16 depicts an example of a block diagram of a biological information detection apparatus according to the embodiment 3. In FIG. 16, like components to those of the example of FIG. 1 are denoted by like reference characters, and overlapping description of them is omitted herein. In the embodiment 3, the detection region signal generation section 400 and the $SpO_2$ calculation section 600 in FIG. 3 are replaced with a detection region signal generation section 400d and a $SpO_2$ calculation section 600d, respectively.

Figure 17:
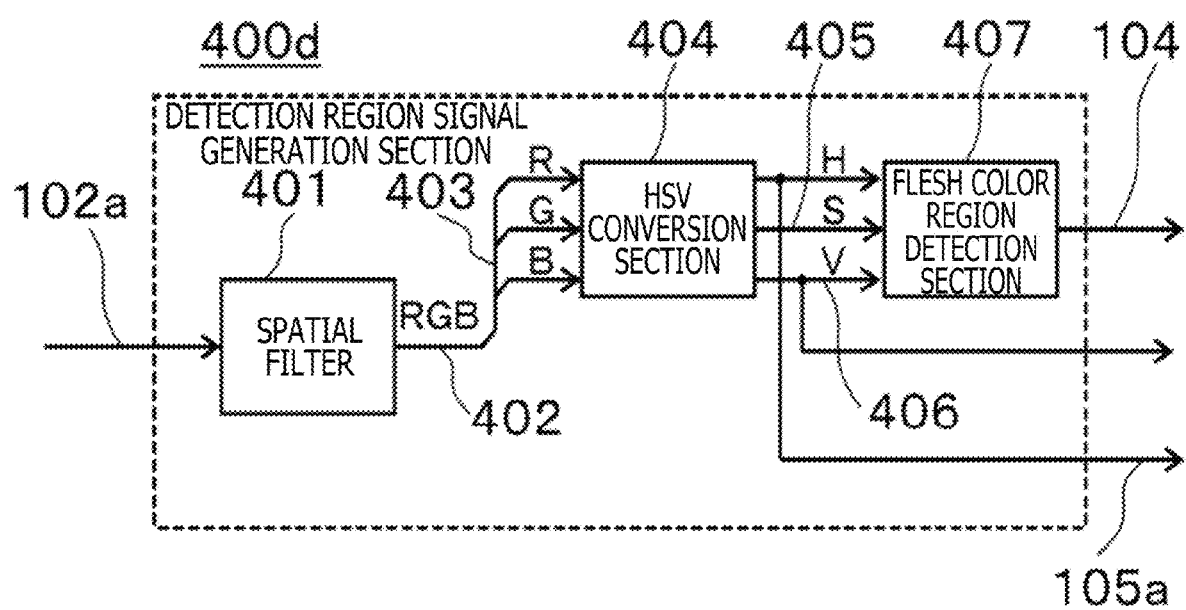
FIG. 17 is a block diagram depicting an example of a detection region signal generation section in the embodiment 3.

FIG. 17 is a view depicting an example of the detection region signal generation section 400d of FIG. 16. In FIG. 17, like components to those of the detection region signal generation section 400 of FIG. 6 are denoted by like reference characters, and overlapping description of them is omitted herein. The detection region signal generation section 400d of the embodiment 3 outputs a V signal (value) 406.

Figure 18:
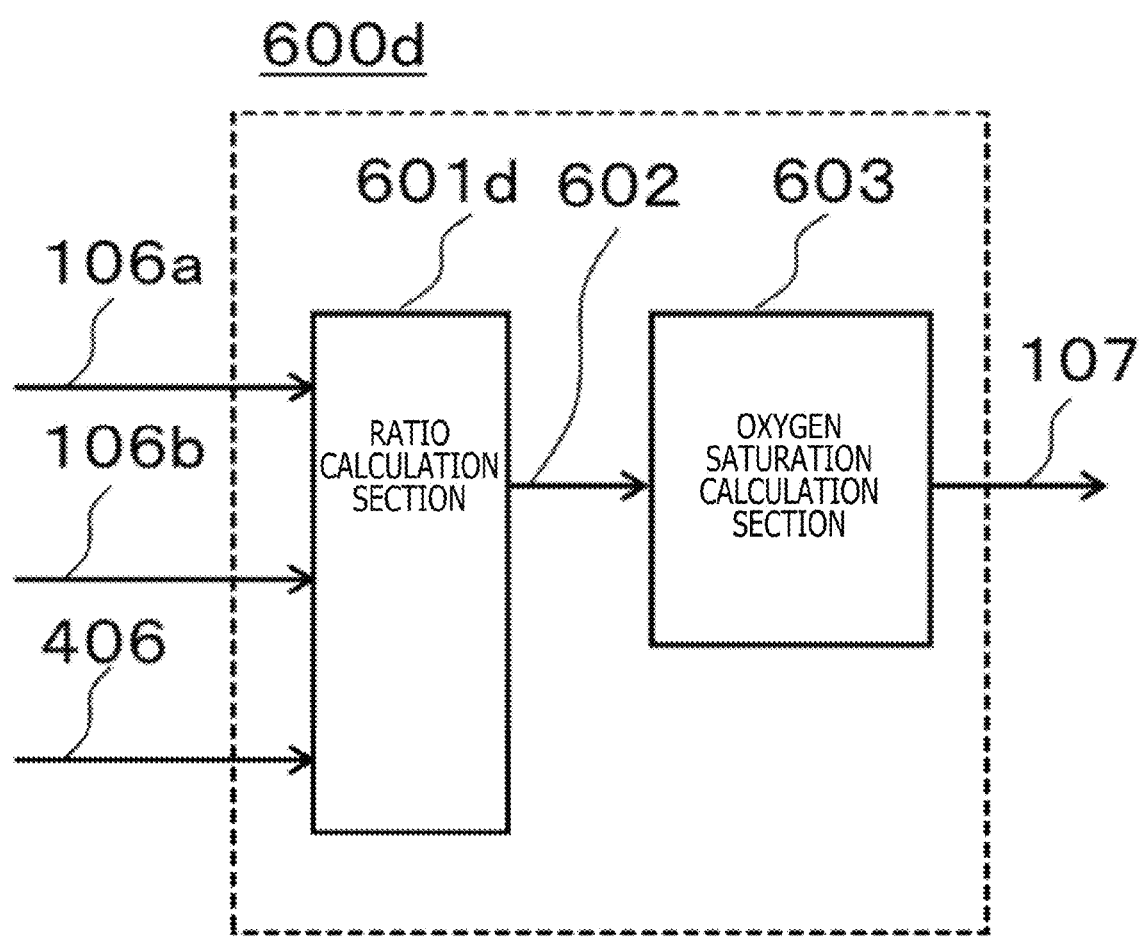
FIG. 18 is a block diagram depicting an example of a SpO₂ detection section in the embodiment 3.

FIG. 18 is a view depicting an example of the $SpO_2$ calculation section 600d of FIG. 16. In FIG. 18, like components to those of the $SpO_2$ calculation section 600 of FIG. 12 are denoted by like reference characters, and overlapping description of them is omitted herein. In the $SpO_2$ calculation section 600d of the embodiment 3, a ratio calculation section 601d receives a V signal (value) 406 in addition to the first amplitude signal (color signal) 106a and the second amplitude signal (IR signal) 106b as input signals thereto.

The ratio calculation section 601d detects an external light variation from a V signal (value) 406 inputted thereto and corrects calculation of the ratio. The ratio calculation section 601d outputs a zero signal when the amplitude signal (color signal) is zero but performs, in any other case, a ratio calculation of an amplitude signal (color signal)/amplitude signal (IR signal), an amplitude signal (IR signal)/(amplitude signal (color signal)+amplitude signal (IR signal)) or the like. Here, the ratio can be corrected by adding, to the amplitude signal (color signal) k (V signal/V0), k and V0 being constants.

In the example described above, the contribution of the V signal (value) 406 is calculated by ratio arithmetic operation. As a different method, the first amplitude signal (color signal) 106a, second amplitude signal (IR signal) 106b and V signal (value) 406 may be inputted such that a ratio is determined by referring to a table that retains three-dimensional arrays for deriving a ratio that is determined uniquely. Alternatively, a ratio of an amplitude signal (color signal)/amplitude signal (IR signal), an amplitude signal (IR signal)/(amplitude signal (color signal)+amplitude signal (IR signal)) or the like and the V signal (value) 406 may be inputted such that a ratio is determined by referring to a table that retains two-dimensional arrays for deriving a ratio that is determined uniquely.

Setting of correction can be performed by using, as an interface, a switch for enabling an external light correction function and a level adjustment function for determining a correction sensitivity. The level adjustment function can make it possible to select a constant or a table described hereinabove. By the configuration described, correction with an influence of external light taken into consideration can be performed and an error upon calculation of a $SpO_2$ can be reduced.

As described above, although a general pulse oximeter is a contact type apparatus that is mounted on a fingertip and irradiates infrared light (IR) and red light on a finger from above to measure an absorption amount of hemoglobin by a sensor to acquire an arterial blood oxygen saturation ($SpO_2$). However, it is difficult for a person to perform measurement while keeping the pulse oximeter mounted thereon during driving of a vehicle or in daily life. According to the embodiments described above, they include a pulse wave detection section that estimates two pulse waves from interframe differences between image signals captured by infrared and visible light cameras and image signals preceding by one frame, and a $SpO_2$ calculation section that calculates the ratio in magnitude between the two generated pulse waves and converts the ratio into an arterial blood oxygen saturation with reference to a correlation table that indicates a relationship between the calculated amplitude ratio and an oxygen saturation concentration such that it makes contactless measurement possible. Therefore, a monitoring technique can be provided by which a condition sudden change of a subject by respiratory disease, heart failure or the like is detected with non-contact.

What is claimed is:

1. A biological information detection apparatus, comprising:

a camera that acquires an image with visible light and infrared light;

a detection region signal generation section that detects a color region of skin of a patient based on the image acquired with the visible light and decomposes an image signal captured by the camera into a wavelength of an image and a spectrum intensity;

a first wavelength fluctuation detection section that detects a temporal variation of a wavelength of an image with the visible light to generate a first wavelength difference data signal, and determines the color region as a target region of variation detection of the wavelength;

a first amplitude detection section that detects an amplitude of the first wavelength difference data signal;

a second wavelength fluctuation detection section that detects a temporal variation of a wavelength of an image with the infrared light to generate a second wavelength difference data signal;

a second amplitude detection section that detects an amplitude of the second wavelength difference data signal;

a ratio calculation section that calculates a ratio between the amplitude of the first wavelength difference data signal and the amplitude of the second wavelength difference data signal; and an oxygen saturation concentration calculation section that calculates an oxygen saturation concentration based on the calculated ratio between the amplitudes, wherein the detection region signal generation section performs the decomposition into the wavelength of the image and the spectrum intensity by converting the image signal into a signal of an HSV color space such that a hue is a wavelength and a value is a spectrum intensity, and the oxygen saturation concentration calculation section corrects the calculation of the oxygen saturation intensity using the value as a signal representative of an intensity of the light.

2. The biological information detection apparatus according to claim 1, wherein
the oxygen saturation concentration calculation section converts the corrected ratio into an oxygen saturation concentration based on a correlation table indicative of a relationship between the corrected calculated ratio in amplitude and the oxygen saturation concentration.

3. The biological information detection apparatus according to claim 1, wherein
also, the second wavelength fluctuation detection section determines the color region as a target region of variation detection of the wavelength.

4. The biological information detection apparatus according to claim 1, wherein
the detection region signal generation section performs the decomposition into a wavelength of an image and a spectrum intensity by converting the image signal into a signal of an HSV color space such that a hue is a wavelength and a value is a spectrum intensity.

5. The biological information detection apparatus according to claim 1, wherein
not a plurality of cameras individually ready for infrared light and visible light are used but a single camera having a filter capable of acquiring infrared light and visible light at the same time is used as the camera such that components of infrared light and visible light are extracted based on pixel values.

6. The biological information detection apparatus according to claim 1, wherein the biological information detection apparatus does not touch the patient.

7. A biological information detection method, comprising:
acquiring a biological image with visible light;
acquiring a biological image with infrared light;
detecting a region of a color of skin of the biological body from the image of the visible light;
decomposing an image signal into a wavelength of an image and a spectrum intensity by converting the image signal into a signal of an HSV color space such that a hue is a wavelength and a value is a spectrum intensity;
detecting a temporal variation of a wavelength of an image with the visible light to generate a first wavelength difference data signal, and a region from which the temporal variation of a wavelength is to be detected is restricted to the region of the color of the skin of the biological body;
detecting an amplitude of the first wavelength difference data signal;
a fifth step of detecting a temporal variation of a wavelength of an image with the infrared light to generate a second wavelength difference data signal, and a region from which the temporal variation of a wavelength is to be detected is restricted to the region of the color of the skin of the biological body;
detecting an amplitude of the second wavelength difference data signal;
calculating a ratio between the amplitude of the first wavelength difference data signal and the amplitude of the second wavelength difference data signal;
correcting the calculation of the oxygen saturation intensity using the value as a signal representative of an intensity of the light; and
estimating information of a biological body based on the corrected calculated ratio between the amplitudes.

8. The biological information detection method according to claim 7, wherein
a memory in which a table that associates the ratio of the amplitude with an oxygen saturation concentration each other is used, and
the oxygen saturation concentration is estimated by referring to the table.

9. The biological information detection method according to claim 7, wherein
information of brightness is acquired from the image of the biological body acquired using the visible light, and an estimation process of the information of the biological body at the eighth step is corrected based on the information of the brightness.

* * * * *